(12) United States Patent
Tseng (10) Patent No.: US 6,931,679 B1
(45) Date of Patent: Aug. 23, 2005

(54) FOLDABLE STAND FOR A HAMMOCK

(75) Inventor: Chuen-Jong Tseng, Chiayi Hsien (TW)

(73) Assignee: Taiwan Shin Yeh Enterprise Co., Ltd., Chiayi Hsien (TW)

( * ) Notice: Subject to any disclaimer, the term of this patent is extended or adjusted under 35 U.S.C. 154(b) by 0 days.

(21) Appl. No.: 10/888,837

(22) Filed: Jul. 9, 2004

(51) Int. Cl.[7] .............................................. A45F 3/24
(52) U.S. Cl. ............................................. 5/127; 5/129
(58) Field of Search ............................. 5/127, 120, 129

(56) References Cited

U.S. PATENT DOCUMENTS

| | | | |
|---|---|---|---|
| 3,593,352 A | * | 7/1971 | Britt ................................. 5/127 |
| 4,925,138 A | * | 5/1990 | Rawlins ........................ 248/165 |
| 5,003,652 A | * | 4/1991 | Bayless ........................... 5/129 |
| 5,297,302 A | * | 3/1994 | Anderson ........................ 5/127 |
| 5,392,476 A | * | 2/1995 | Williams ......................... 5/127 |
| 5,659,907 A | * | 8/1997 | Huang ............................ 5/128 |
| 5,983,422 A | * | 11/1999 | Bayless .......................... 5/120 |

* cited by examiner

*Primary Examiner*—Robert G. Santos
(74) *Attorney, Agent, or Firm*—Ladas & Parry LLP (57) ABSTRACT

A foldable hammock stand includes an elongate base that has opposite left and right end portions, a pair of first lateral members coupled pivotally to the left end portion of the elongate base, a pair of second lateral members coupled pivotally to the right end portion of the elongate base, and a pair of posts coupled pivotally and respectively to the left and right end portions of the elongate base.

7 Claims, 6 Drawing Sheets

FIG. 6

FOLDABLE STAND FOR A HAMMOCK

BACKGROUND OF THE INVENTION

1. Field of the Invention

The invention relates to a hammock stand, more particularly to a foldable hammock stand.

2. Description of the Related Art

Typically, hammocks are suspended above the ground between trees, posts, and other relatively stable supporting structures. However, these supporting structures do not normally exist in areas which are most desirable for the use of a hammock. A conventional hammock stand has been proposed to alleviate this drawback.

Although the conventional hammock stand achieves its intended purpose, since the conventional hammock stand includes numerous parts, this arises in inconvenience on the part of the user during assembling and disassembling. Furthermore, these parts are easily misplaced during disassembly and storage.

SUMMARY OF THE INVENTION

Therefore, the object of the present invention is to provide a foldable hammock stand that is capable of overcoming the aforesaid drawbacks of the prior art.

According to the present invention, a foldable stand, which is for suspending a hammock above the ground, includes a base unit and a pair of posts. The base unit includes an elongate base, a pair of first lateral members, and a pair of second lateral members. The elongate base has opposite left and right end portions. Each of the left and right end portions of the elongate base has opposite front and rear walls, and a top wall that interconnects the front and rear walls of a respective one of the left and right end portions of the elongate base. Each of the first lateral members is coupled pivotally to a respective one of the front and rear walls of the left end portion of the elongate base. Each of the first lateral members is pivotable relative to the elongate base to a first unfolded position, where each of the first lateral members is disposed generally transverse to the respective one of the front and rear walls of the left end portion of the elongate base. Each of the second lateral members is coupled pivotally to a respective one of the front and rear walls of the right end portion of the elongate base. Each of the second lateral members is pivotable relative to the elongate base to a second unfolded position, where each of the second lateral members is disposed generally transverse to the respective one of the front and rear walls of the right end portion of the elongate base. Each of the posts is coupled pivotally to the top wall of a respective one of the left and right end portions of the elongate base. Each of the posts is pivotable relative to the elongate base to a third unfolded position, where each of the posts forms an angle with the top wall of the respective one of the left and right end portions of the elongate base. The posts are adapted to support the hammock when the posts are disposed at the third unfolded position.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
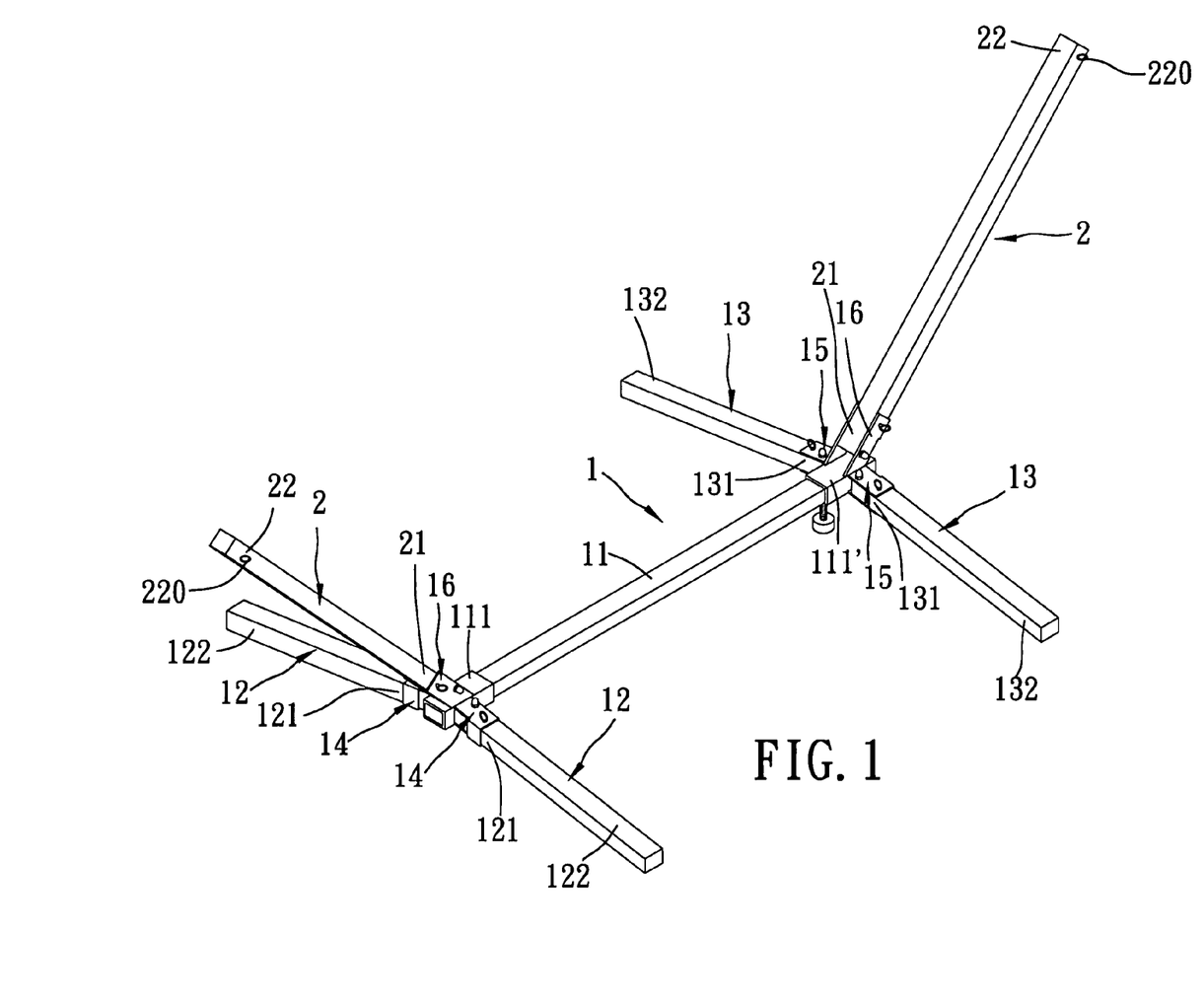
FIG. 1 is a perspective view of the preferred embodiment of a foldable stand according to the present invention.
Figure 2:
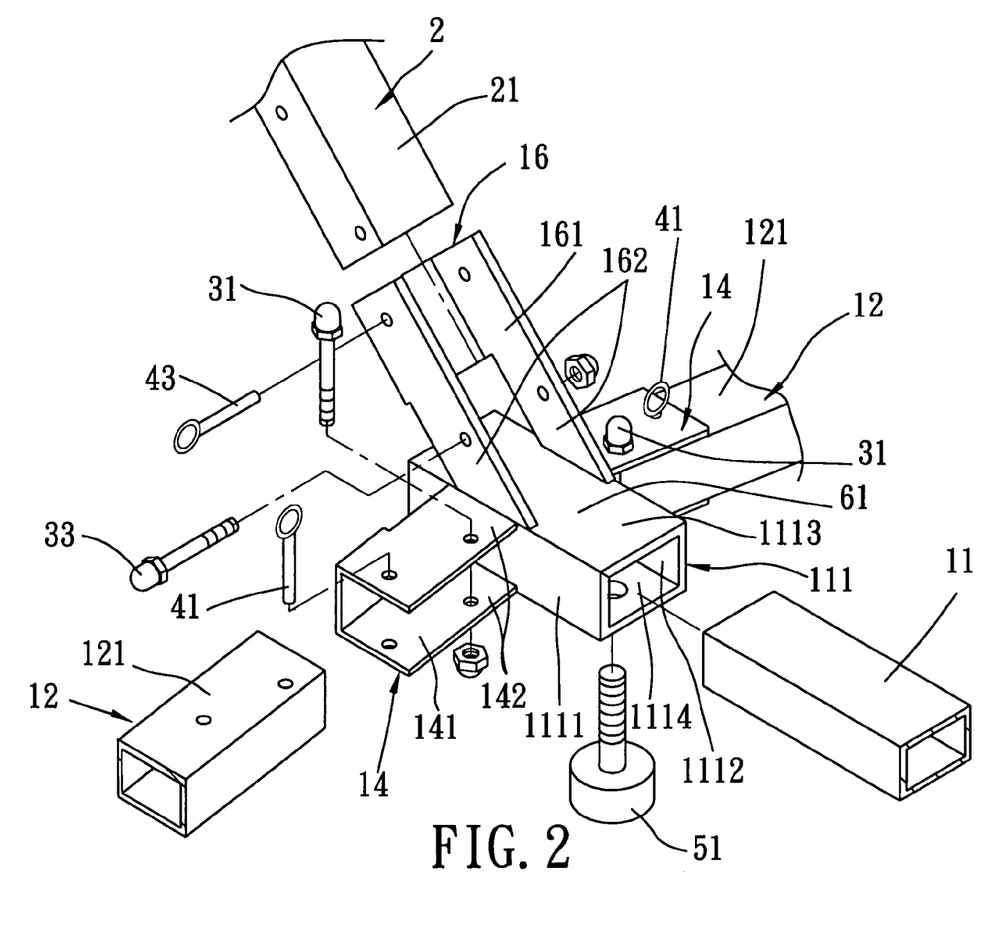
FIG. 2 is a fragmentary exploded perspective view to illustrate a left end portion of the preferred embodiment.
Figure 3:
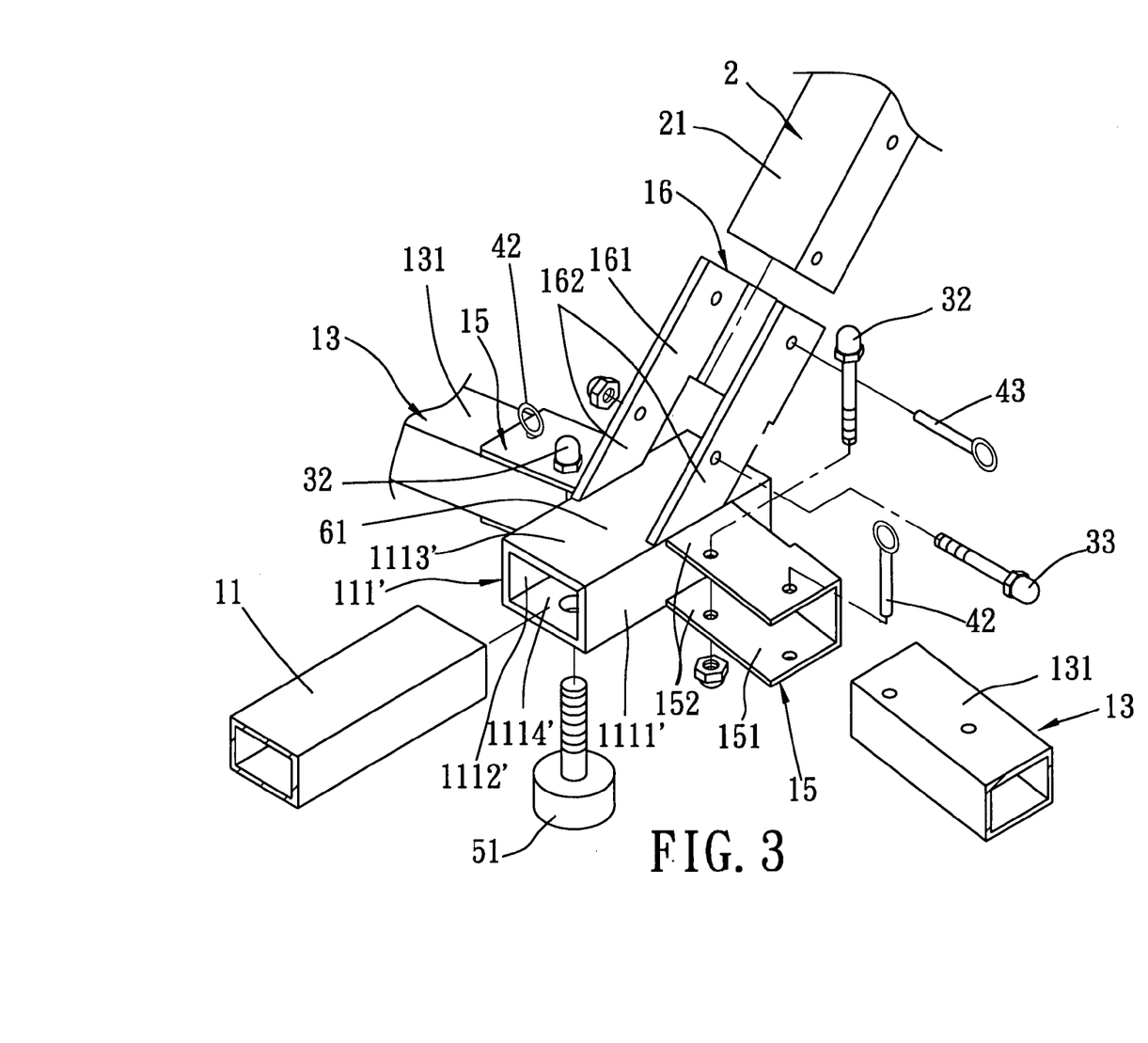
FIG. 3 is a fragmentary exploded perspective view to illustrate a right end portion of the preferred embodiment.

Referring to FIGS. 1 to 3, the preferred embodiment of a foldable stand according to this invention is shown to include a base unit 1 and a pair of posts 2.

The foldable stand of this embodiment is adapted to suspend a hammock (not shown) above the ground (not shown).

The base unit 1 includes an elongate base 11, a pair of first lateral members 12, and a pair of second lateral members 13.

The elongate base 11 has opposite left and right end portions 111, 111'. Each of the left and right end portions 111, 111' of the elongate base 11 has opposite front and rear walls 1111, 1111', 1112, 1112', a top wall 1113, 1113' that interconnects the front and rear walls 1111, 1111', 1112, 1112' of a respective one of the left and right end portions 111, 111' of the elongate base 11, and a bottom wall 1114, 1114' that is opposite to the top wall 1113, 1113' of a respective one of the left and right end portions 111, 111' of the elongate base 11 and that interconnects the front and rear walls 1111, 1111', 1112, 1112' of the respective one of the left and right end portions 111, 111' of the elongate base 11.

In this embodiment, the base unit 1 further includes a pair of sleeve members 61, each of which is sleeved on the elongate base 11 and serves as a respective one of the left and right end portions 111, 111' of the elongate base 11. In an alternative embodiment, the sleeve members may be dispensed with.

Each of the first lateral members 12 has a pivot end portion 121, and a free end portion 122 opposite to the pivot end portion 121 of a respective one of the first lateral members 12. The pivot end portion 121 of each of the first lateral members 12 is coupled pivotally to a respective one of the front and rear walls 1111, 1112 of the left end portion 111 of the elongate base 11.

In this embodiment, each of the first lateral members 12 is pivotable relative to the elongate base 11 between a first unfolded position, where each of the first lateral members 12 is disposed generally transverse to the respective one of the front and rear walls 1111, 1112 of the left end portion 111 of the elongate base 11, and a first folded position, where each of the first lateral members 12 is juxtaposed to the respective one of the front and rear walls 1111, 1112 of the left end portion 111 of the elongate base 11.

Each of the second lateral members 13 has a pivot end portion 131, and a free end portion 132 opposite to the pivot end portion 131 of a respective one of the second lateral members 13. The pivot end portion 131 of each of the second lateral members 13 is coupled pivotally to a respective one of the front and rear walls 1111', 1112' of the right end portion 111' of the elongate base 11.

In this embodiment, each of the second lateral members 13 is pivotable relative to the elongate base 11 between a second unfolded position, where each of the second lateral members 13 is disposed generally transverse to the respective one of the front and rear walls 1111', 1112' of the right end portion 111' of the elongate base 11, and a second folded position, where each of the second lateral members 13 is juxtaposed to the respective one of the front and rear walls 1111', 1112' of the right end portion 111' of the elongate base 11.

Each of the posts 2 has a pivot end portion 21, and a free end portion 22 opposite to the pivot end portion 21 of a respective one of the posts 2. The pivot end portion 21 of each of the posts 2 is coupled pivotally to the top wall 1113, 1113' of a respective one of the left and right end portions 111, 111' of the elongate base 11.

In this embodiment, each of the posts 2 is pivotable relative to the elongate base 11 between a third unfolded position, where each of the posts 2 forms an angle with the top wall 1113, 1113' of the respective one of the left and right end portions 111, 111' of the elongate base 11, and a third folded position, where each of the posts 2 is juxtaposed to the top wall 1113, 1113' of the respective one of the left and right end portions 111, 111' of the elongate base 11.

The base unit 1 further includes a pair of first mounting brackets 14, a pair of second mounting brackets 15, and a pair of third mounting brackets 16.

Each of the first mounting brackets 14 has a first end portion 141, and a second end portion 142 opposite to the first end portion 141 of a respective one of the first mounting brackets 14. The second end portion 142 of each of the first mounting brackets 14 has a distal end that is distal from the first end portion 141 of the respective one of the first mounting brackets 14 and that is connected securely to the respective one of the front and rear walls 1111, 1112 of the left end portion 111 of the elongate base 11. The second end portion 142 of each of the first mounting brackets 14 is connected pivotally to the pivot end portion 121 of a respective one of the first lateral members 12. The first end portion 141 of each of the first mounting brackets 14 has a U-shaped cross-section, and includes a pair of parallel arms and a cross arm. The second end portion 142 of each of the first mounting brackets 14 includes parallel arms that extend respectively from the parallel arms of the first end portion 141 of the respective one of the first mounting brackets 14.

It is noted that each of the first mounting brackets 14 is inclined slightly and downwardly from the respective one of the front and rear walls 1111, 1112 of the left end portion 111 of the elongate base 11.

Each of the second mounting brackets 15 has a first end portion 151, and a second end portion 152 opposite to the first end portion 151 of a respective one of the second mounting brackets 15. The second end portion 152 of each of the second mounting brackets 15 has a distal end that is distal from the first end portion 151 of the respective one of the second mounting brackets 15 and that is connected securely to the respective one of the front and rear walls 1111', 1112' of the right end portion 111' of the elongate base 11. The second end portion 152 of each of the second mounting brackets 15 is connected pivotally to the pivot end portion 131 of the respective one of the second lateral members 13. The first end portion 151 of each of the second mounting brackets 15 has a U-shaped cross-section, and includes a pair of parallel arms and a cross arm. The second end portion 152 of each of the second mounting brackets 15 includes parallel arms that extend respectively from the parallel arms of the first end portion 151 of the respective one of the second mounting brackets 15.

It is noted that each of the second mounting brackets 15 is inclined slightly and downwardly from the respective one of the front and rear walls 1111', 1112' of the right end portion 111' of the elongate base 11.

Each of the third mounting brackets 16 has a first end portion 161, and a second end portion 162 opposite to the first end portion 161 of a respective one of the third mounting brackets 16. The second end portion 162 of each of the third mounting brackets 16 has a distal end that is distal from the first end portion 161 of the respective one of the third mounting brackets 16 and that is connected securely to the top wall 1113, 1113' of the respective one of the left and right end portions 111, 111' of the elongate base 11. The second end portion 162 of each of the third mounting brackets 16 is connected pivotally to the pivot end portion 21 of a respective one of the posts 2. The first end portion 161 of each of the third mounting brackets 16 has a U-shaped cross-section, and includes a pair of parallel arms and a cross arm. The second end portion 162 of each of the third mounting brackets 16 includes parallel arms that extend respectively from the parallel arms of the first end portion 161 of the respective one of the third mounting brackets 16.

It is noted that the third mounting brackets 16 are inclined upwardly from the elongate base 11 in such a manner that the posts 2 extend upwardly, inclinedly and away from each other when the posts 2 are disposed at the third unfolded position.

It is also noted that the pivot end portion 21 of each of the posts 2 abuts against the cross arm of the first end portion 161 of the respective one of the third mounting brackets 16 when the posts 2 are disposed at the third unfolded position.

It is further noted that the posts 2 are adapted to support the hammock when the posts 2 are disposed at the third unfolded position. In particular, the free end portion 22 of each of the posts 2 is provided with a loop 220 that is fastened to a respective one of first and second ends of the hammock.

The foldable stand further includes a pivot unit. The pivot unit includes a pair of first pivot pins 31, a pair of second pivot pins 32, and a pair of third pivot pins 33. The pivot end portion 121 of each of the first lateral members 12 is pivoted to the second end portion 142 of the respective one of the first mounting brackets 14 through a respective one of the first pivot pins 31. The pivot end portion 131 of each of the second lateral members 13 is pivoted to the second end portion 152 of the respective one of the second mounting brackets 15 through a respective one of the second pivot pins 32. The pivot end portion 21 of each of the posts 2 is pivoted to the second end portion 162 of the respective one of the third mounting brackets 16 through a respective one of the third pivot pins 33.

The foldable stand further includes a retaining unit. The retaining unit includes first, second, and third retainers. The first retainer fastens each of the first lateral members 12 to of the respective one of the first mounting brackets 14 to retain the first lateral members 12 at the first unfolded position. In this embodiment, the first retainer includes a pair of first locking pins 41, each of which extends removably through the first end portion 141 of a respective one of the first mounting brackets 14 and the pivot end portion 121 of a respective one of the first lateral members 12. The second retainer fastens each of the second lateral members 13 to the respective one of the second mounting brackets 15 to retain the second lateral members 13 at the second unfolded position. In this embodiment, the second retainer includes a pair of second locking pins 42, each of which extends removably through the first end portion 151 of a respective one of the second mounting brackets 15 and the pivot end portion 131 of a respective one of the second lateral members 13. The third retainer fastens each of the posts 2 to the respective one of the third mounting brackets 16 to retain the posts 2 at the third unfolded position. In this embodiment, the third retainer includes a pair of third locking pins 43, each of which extends removably through the first end portion 161 of a respective one of the third mounting brackets 16 and the pivot end portion 21 of a respective one of the posts 2.

Figure 4:
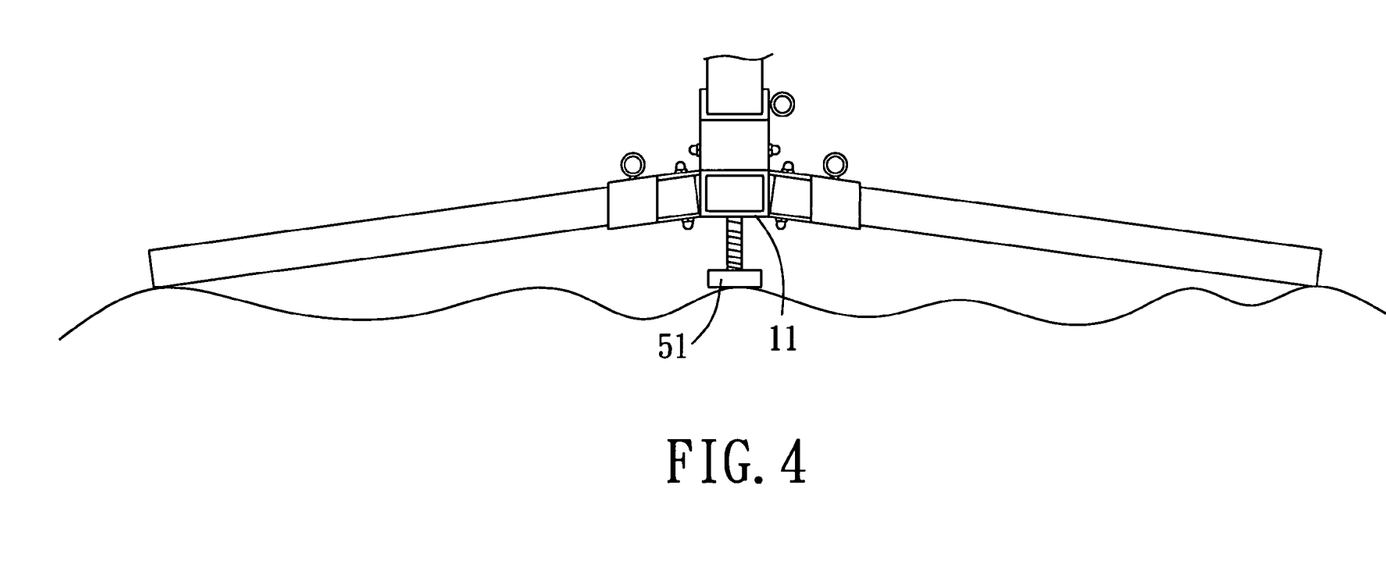
FIG. 4 is a schematic view to illustrate how a level-adjusting unit of the preferred embodiment is operated.

The base unit further includes a pair of level-adjusting members, each of which includes a screw rod 51 that threadedly engages the bottom wall 1114, 1114' of a respective one of the left and right end portions 111, 111' of the elongate base 11. Each of the screw rods 51 is adjustable, in a known manner, so as to support the elongate base 11 on an uneven ground, as best shown in FIG. 4.

Figure 5:
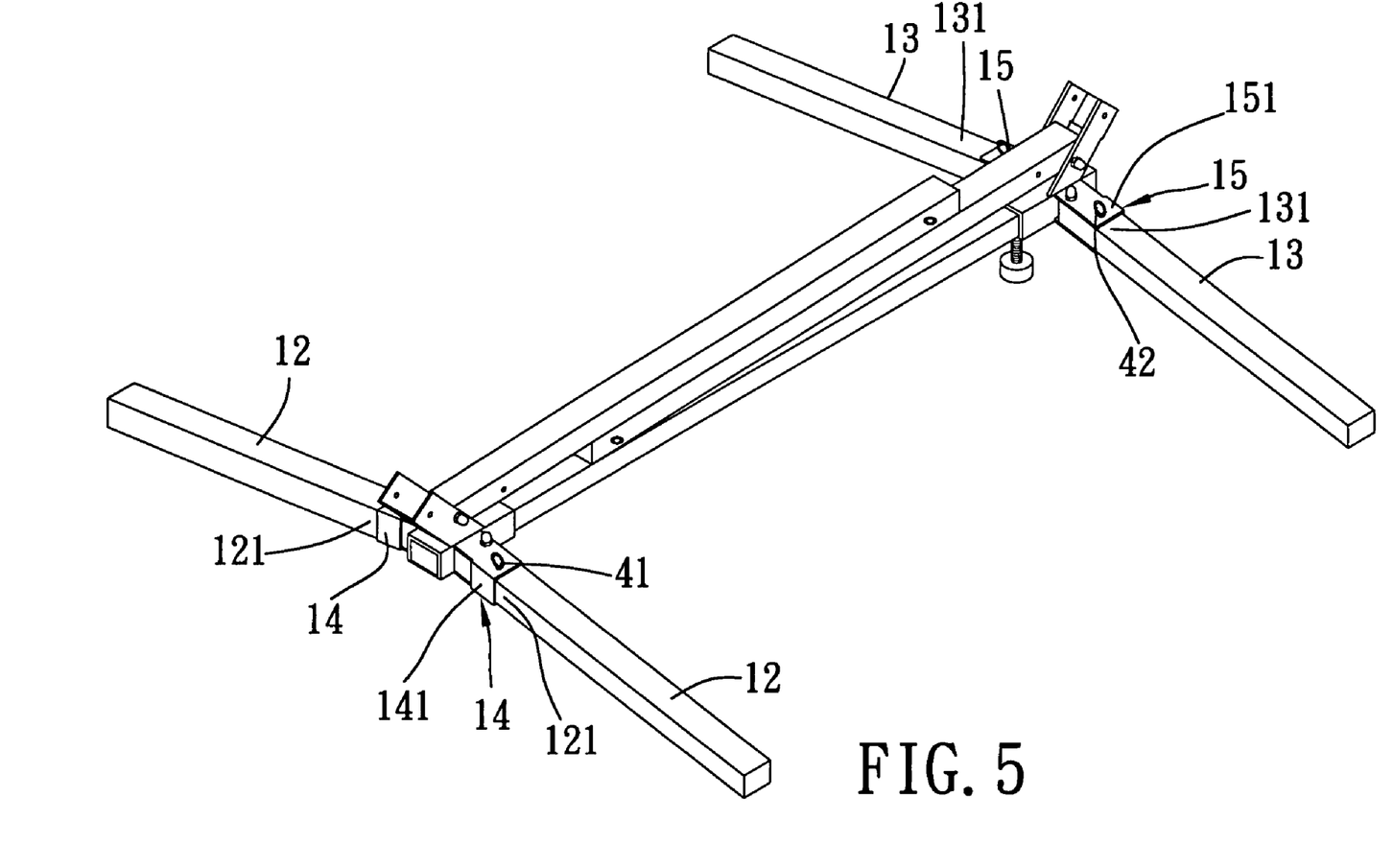
FIG. 5 is a perspective view to illustrate a state where first and second lateral members of the preferred embodiment are disposed at an unfolded position, and where posts of the preferred embodiment are disposed at a folded position.
Figure 6:
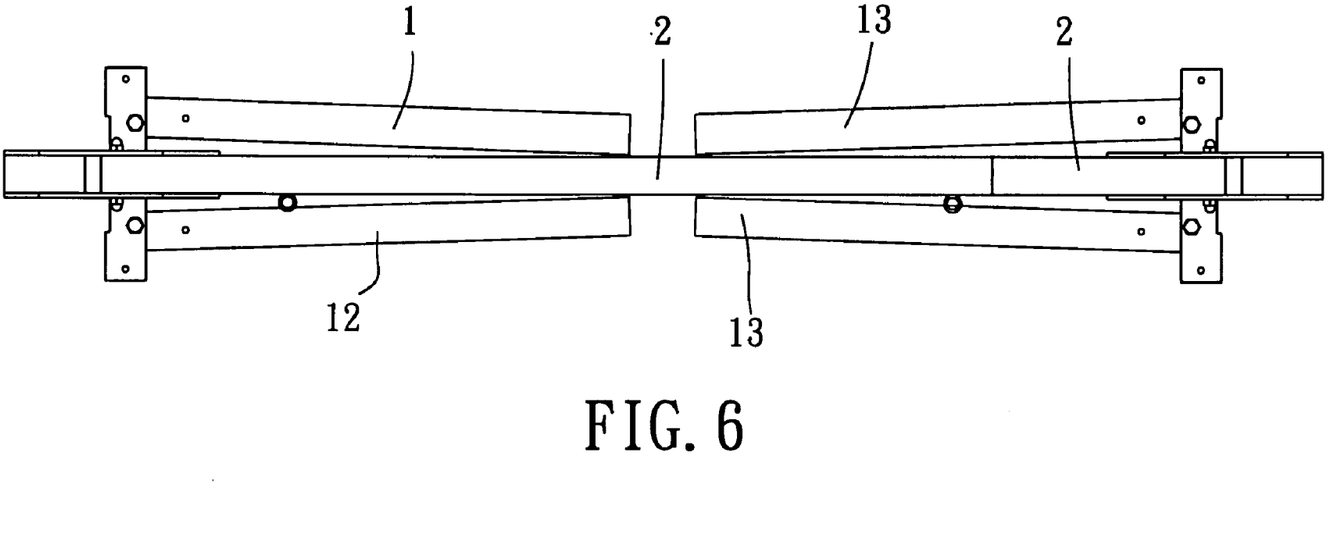
FIG. 6 is a top view to illustrate a state where the first and second lateral members, and the posts of the preferred embodiment are all disposed at a folded position.

Referring to FIG. 5, when it is desired to fold the foldable stand, firstly, each of the third locking pins 43 (see FIGS. 2 and 3) is removed. Then, each of the posts 2 is disposed at the third folded position. Secondly, with further reference to FIG. 6, each of the first locking pins 41 (see FIGS. 2 and 3) is removed. Then, each of the first lateral members 12 is disposed at the first folded position. Finally, each of the second locking pins 42 (see FIGS. 2 and 3) is removed. Then, each of the second lateral members 13 is disposed at the second folded position.

It has thus been shown that the foldable stand of this invention includes an elongate base 11, a pair of first lateral members 12, each of which is coupled pivotally to a left end portion 111 of the elongate base 11, a pair of second lateral members 15, each of which is coupled pivotally to a right end portion 111' of the elongate base 11, and a pair of posts 2, each of which is coupled pivotally to a respective one of the left and right end portions 111, 111' of the elongate base 11. As such, the foldable stand can be easily and conveniently folded to facilitate transport or storage.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A foldable stand for suspending a hammock above the ground, said foldable stand comprising:
    a base unit including
       an elongate base that has opposite left and right end portions, each of said left and right end portions of said elongate base having opposite front and rear walls, and a top wall that interconnects said front and rear walls of a respective one of said left and right end portions of said elongate base,
       a pair of first lateral members, each of which is coupled pivotally to a respective one of said front and rear walls of said left end portion of said elongate base, each of said first lateral members being pivotable relative to said elongate base to a first unfolded position, where each of said first lateral members is disposed generally transverse to the respective one of said front and rear walls of said left end portion of said elongate base, and
       a pair of second lateral members, each of which is coupled pivotally to a respective one of said front and rear walls of said right end portion of said elongate base, each of said second lateral members being pivotable relative to said elongate base to a second unfolded position, where each of said second lateral members is disposed generally transverse to the respective one of said front and rear walls of said right end portion of said elongate base; and
       a pair of posts, each of which is coupled pivotally to said top wall of a respective one of said left and right end portions of said elongate base, each of said posts being pivotable relative to said elongate base to a third unfolded position, where each of said posts forms an angle with said top wall of the respective one of said left and right end portions of said elongate base, said posts being adapted to support the hammock when said posts are disposed at the third unfolded position; wherein each of said left and right end portions of said elongate base further has a bottom wall, said bottom wall being opposite to said top wall and interconnecting said front and rear walls of the respective one of said left and right end portions of said elongate base,
    said base unit further including a pair of level-adjusting members, each of which includes a screw rod that threadedly engages said bottom wall of a respective one of said left and right end portions of said elongate base.

2. The foldable stand as claimed in claim 1, wherein said base unit further includes
    a pair of first mounting brackets connected securely and respectively to said front and rear walls of said left end portion of said elongate base, and connected pivotally and respectively to said first lateral members,
    a pair of second mounting brackets connected securely and respectively to said front and rear walls of said right end portion of said elongate base, and connected pivotally and respectively to said second lateral members, and
    a pair of third mounting brackets connected securely and respectively to said top walls of said left and right end portions of said elongate base, and connected pivotally and respectively to said posts.

3. The foldable stand as claimed in claim 2, further comprising:
    a retaining unit including
       a first retainer that fastens each of said first lateral members to the respective one of said first mounting brackets to retain said first lateral members at the first unfolded position,
       a second retainer that fastens each of said second lateral members to the respective one of said second mounting brackets to retain said second lateral members at the second unfolded position, and
       a third retainer that fastens each of said posts to the respective one of said third mounting brackets to retain said posts at the third unfolded position.

4. The foldable stand as claimed in claim 3, wherein said first retainer includes a pair of first locking pins, each of which extends removably through a respective one of said first mounting brackets and a respective one of said first lateral members,
    said second retainer including a pair of second locking pins, each of which extends removably through a respective one of said second mounting brackets and a respective one of said second lateral members,
    said third retainer including a pair of third locking pins, each of which extends removably through a respective one of said third mounting brackets and a respective one of said posts.

5. The foldable stand as claimed in claim 1, wherein said base unit further includes a pair of sleeve members, each of which is sleeved on said elongate base and serves as a respective one of said left and right end portions of said elongate base.

6. The foldable stand as claimed in claim 1, wherein said posts extend upwardly, inclinedly and away from each other when said posts are disposed at the third unfolded position.

7. The foldable stand as claimed in claim 1, wherein each of said first lateral members is further pivotable relative to said elongate base to a first folded position, where said first lateral members are juxtaposed to said elongate base,     each of said second lateral members being further pivotable relative to said elongate base to a second folded position, where said second lateral members are juxtaposed to said elongate base,     each of said posts being further pivotable relative to said elongate base to a third folded position, where said posts are juxtaposed to said elongate base.

\* \* \* \* \*